United States Patent [19]

Whitehead et al.

[11] Patent Number: 4,554,088
[45] Date of Patent: Nov. 19, 1985

[54] MAGNETIC PARTICLES FOR USE IN SEPARATIONS

[75] Inventors: Roy A. Whitehead, Hingham; Mark S. Chagnon, Lowell; Ernest V. Groman, Brookline; Lee Josephson, Arlington, all of Mass.

[73] Assignee: Advanced Magnetics Inc., Cambridge, Mass.

[21] Appl. No.: 493,991

[22] Filed: May 12, 1983

[51] Int. Cl.[4] .......................... C04B 35/04; H01F 1/26
[52] U.S. Cl. .............................. 252/62.54; 252/62.51; 427/127; 428/405; 436/526; 436/527
[58] Field of Search ........................ 252/62.54, 62.51; 436/526, 527

[56] References Cited

U.S. PATENT DOCUMENTS

| | | |
|---|---|---|
| 3,180,741 | 4/1965 | Wainer et al. . |
| 3,215,572 | 11/1965 | Papell . |
| 3,352,638 | 11/1967 | Perlowski . |
| 3,470,067 | 9/1969 | Warren et al. . |
| 3,480,555 | 11/1969 | Jackson et al. . |
| 3,498,748 | 3/1970 | Greiner . |
| 3,573,980 | 4/1971 | Haller et al. . |
| 3,632,512 | 1/1972 | Miller . |
| 3,650,698 | 3/1972 | Adler . |
| 3,652,761 | 3/1972 | Weetall . |
| 3,700,555 | 10/1972 | Widmark et al. . |
| 3,700,595 | 10/1972 | Kaiser . |
| 3,718,594 | 2/1973 | Miller . |
| 3,736,500 | 5/1973 | Berkowitz et al. . |
| 3,764,540 | 10/1973 | Khalafalla et al. . |
| 3,791,930 | 2/1974 | Saxholm . |
| 3,870,645 | 3/1975 | Frei et al. . |
| 3,933,997 | 1/1976 | Hersh et al. . |
| 3,981,776 | 9/1976 | Saxholm . |
| 3,985,649 | 10/1976 | Eddelman . |
| 3,996,407 | 12/1976 | Gross et al. . |
| 4,018,886 | 4/1977 | Giaever . |
| 4,070,247 | 1/1978 | Kennedy et al. .................. 252/62.54 |
| 4,078,971 | 3/1978 | Arkles et al. . |
| 4,101,435 | 7/1978 | Hasegawa ........................ 252/62.53 |
| 4,115,534 | 9/1978 | Ithakissios ........................ 252/62.54 |
| 4,115,535 | 9/1978 | Giaever . |
| 4,123,396 | 10/1978 | Rembaum et al. . |
| 4,138,383 | 2/1979 | Rembaum et al. . |
| 4,141,687 | 2/1979 | Forrest et al. . |
| 4,157,323 | 6/1979 | Yen et al. . |
| 4,169,804 | 10/1979 | Yapel ............................... 252/62.54 |
| 4,177,317 | 12/1979 | Schöenfinger et al. . |
| 4,197,220 | 4/1980 | Rembaum et al. . |
| 4,206,094 | 6/1980 | Yen et al. . |
| 4,219,335 | 8/1980 | Ebersole . |
| 4,219,411 | 8/1980 | Yen et al. . |
| 4,241,176 | 12/1980 | Avrameas et al. . |
| 4,247,406 | 1/1981 | Widdler et al. .................. 252/62.53 |
| 4,267,234 | 5/1981 | Rembaum ........................ 252/62.54 |
| 4,267,235 | 5/1981 | Rembaum . |
| 4,272,510 | 6/1981 | Smith et al. . |
| 4,331,654 | 5/1982 | Morris . |
| 4,335,094 | 6/1982 | Mosbach . |
| 4,345,588 | 8/1982 | Widder et al. . |
| 4,356,098 | 10/1982 | Chagnon ........................ 252/62.53 |
| 4,357,259 | 11/1982 | Senyei et al. ..................... 252/62.53 |
| 4,369,226 | 1/1983 | Rembaum . |
| 4,452,773 | 6/1984 | Molday ........................... 252/62.54 |

OTHER PUBLICATIONS

Hersh and Yaverbaum, Clin. Chim. Acta, 63: 69–72 (1975).
Robinson, et al., Biotech, Bioeng., XV: 603–606 (1973).
Guesdon and Avrameas, Immunochemistry, 14: 443–447 (1977).

(List continued on next page.)

Primary Examiner—Arthur P. Demers
Attorney, Agent, or Firm—Pennie & Edmonds

[57] ABSTRACT

A process is provided for the preparation of magnetic particles to which a wide variety of molecules may be coupled. The magnetic particles can be dispersed in aqueous media without rapid settling and conveniently reclaimed from media with a magnetic field. Preferred particles do not become magnetic after application of a magnetic field and can be redispersed and reused. The magnetic particles are useful in biological systems involving separations.

11 Claims, 2 Drawing Figures

OTHER PUBLICATIONS

Kaiser and Miskolczy, J. of Applied Physics, 41(3): 1064–1072.
Molday et al, Nature 268: 437–438 (1977).
Rembaum, Pure & Appl. Chem. 52: 1275–1278 (1980).
Rembaum and Margel, T. British Polymer Journal 10: 275–280 (Dec. 1978).
Rembaum and Yen, J. Macromol. Sci.–Chem., A13(5): 603–632 (1979).
Rembaum et al., Chemtech, 182–190 (Mar. 1978).
Carter, Clin. Chem 24:362–364 (1978).
Dawes and Gardner, Clin. Chim. Acta 86: 353–356 (1978).
Freifelder, Physical Biochemistry: Applications to Biochemistry and Molecular Biology, p. 259, W. H. Freeman and Company, San Francisco (1976).
Guesdon et al., J. Allergy Clin. Immunol. 61(1): 23–27 (1978).
Halling and Dunnill, Enzyme Microb. Technol. 2: 2–10 (1980).
Hirschbein et al., Chemtech, Mar. 1982: 172–179 (1982).
Ithakissios and Kubiatowicz, Clin. Chem. 23(11): 2072–2079 (1977).
Ithakissios et al., Clin. Chim. Acta, 84: 69–84 (1978).
Jacobs, The Ligand Quarterly, 4(4): 23–33 (1981).
Kamel and Gardner, Clin. Chim. Acta, 89: 363–370 (1978).
Kamel et al., Clin. Chem., 25(12): 1997–2002 (1979).
Kamel et al., Clin. Chem., 26(9): 1281–1284 (1980).
Klibanov, Science, 219: 722 (1983).
Mosbach and Anderson, Nature, 270: 259–261 (1977).
Nayak, The Ligand Quarterly 4(4): 34 (1981).
Nye et al., Clin. Chim. Acta, 69: 387–396 (1976).
Parsons, in: Methods in Enzymology, J. Langone (ed.) 73: 224–239 (1981).
Pourfarzaneh, The Ligand Quarterly 5(1): 41–47 (1982).
Pourfarzaneh et al., Clin. Chem., 26(6): 730–733 (1980).
Weetall, in: Methods in Enzymology, K. Mosbach (ed.), 44: 134–148 (1976).

MAGNETIC PARTICLES FOR USE IN SEPARATIONS

TABLE OF CONTENTS

1. Field of the Invention
2. Background of the Invention
   2.1. Magnetic Separations in Biological Systems: General Considerations
   2.2. Separations in Radioimmunoassays
   2.3. Application of Magnetic Separations in Other Biological Systems
3. Nomenclature
4. Summary of the Invention
5. Brief Description of the Figures
6. Detailed Description of the Invention
   6.1. Magnetic Particle Preparation
   6.2. Silane Coupling Chemistry
   6.3. Use of Magnetic particles in Biological
   6.4. Use of Magnetic Particles in Immobilized Enzyme Systems
   6.5. Use of Magnetic Particles in Affinity Chromatography
7. Examples
   7.1. Preparation of Metal Oxide
   7.2. Silanization
   7.3. Physical Characteristics of Silanized Magnetic Particles
   7.4. Coupling of Aminophenyl Magnetic Particles to Antibodies to Thyroxine
   7.5. Magnetic Particle Radioimmunoassay for Thyroxine
   7.6. Magnetic Particle Radioimmunoassay for Theophylline
   7.7. Effect of Variation of $Fe^{2+}/Fe^{3+}$ Ratio of Magnetic Particles on $T_4$ Radioimmunoassay
   7.8. Coupling of Carboxylic Acid-Terminated Magnetic Particles to $B_{12}$ Binding Protein
      7.8.1. Preparation of Carboxylic Acid-Tersinated Magnetic Particles
      7.8.2. Carbodiimide Coupling of $B_{12}$ Binding Protein and Human Serum Alubmin to Carboxylic Acid-Terminated Particles
   7.9. Magnetic Particle Competitive Binding Assay for Vitamin $B_{12}$
   7.10. Coupling of Magnetic particles Coated with 3-Aminopropyl or N-2-Aminoethyl-3-Aminopropyl Silane to Proteins
      7.10.1. Coupling of N-2-Aminoethyl-3-Aminopropyl Magnetic Particles to Antibodies to Triiodothyronine
      7.10.2. Coupling of N-2-Aminoethyl-3-Aminopropyl Magnetic Particles to Antibodies to Thyroid Stimulating Hormone
   7.11 Magnetic Particle Radioimmunoassay for Triiodothyronine
   7.12. Magnetic Particle Radioimmunoassay for Thyroid Stimulating Hormone
   7.13. Coupling of Magnetic Particles Coated with N-2-Aminoethyl-3-Aminopropyl Silane to Enzymes by Use of Glutaraldehyde

1. FIELD OF THE INVENTION

This invention relates to magnetically responsive particles and to their use in systems in which the separation of certain molecules from the surrounding medium is necessary or desirable. More particularly, the invention relates to methods for the preparation of magnetically responsive particles comprising a metal oxide core surrounded by a stable silane coating to which a wide variety of organic and/or biological molecules may be coupled. The particles (coupled or uncoupled) can be dispersed in aqueous media without rapid gravitational settling and conveniently reclaimed from the media with a magnetic field. Preferably, the process provided herein yields particles that are superparamagnetic; that is, they do not become permanently magnetized after application of a magnetic field. This property permits the particles to be redispersed without magnetic aggregate formation. Hence the particles may be reused or recycled. Stability of the silane coating and the covalent attachment of molecules thereto also contribute to particle use and reuse.

The magnetically responsive particles of this invention may be coupled to biological or organic molecules with affinity for or the ability to adsorb or which interact with certain other biological or organic molecules. Particles so coupled may be used in a variety of in vitro or in vivo systems involving separation steps or the directed movement of coupled molecules to particular sites, including, but not limited to, immunological assays, other biological assays, biochemical or enzymatic reactions, affinity chromatographic purifications, cell sorting and diagnostic and therapeutic uses.

2. BACKGROUND OF THE INVENTION

2.1. Magnetic Separations in Biological Systems: General Considerations

The use of magnetic separations in biological systems as an alternative to gravitational or centrifugal separations has been reviewed [B. L. Hirschbein et al., Chemtech, March 1982:172–179 (1982); M. Pourfarzaneh, The Ligand Quarterly 5(1):41–47 (1982); and P. J. Halling and P. Dunnill, Enzyme Microb. Technol. 2:2–10 (1980)]. Several advantages of using magnetically separable particles as supports for biological molecules such as enzymes, antibodies and other bioaffinity adsorbents are generally recognized. For instance, when magnetic particles are used as solid phase supports in immobilized enzyme systems [see, e.g., P. J. Robinson et al., Biotech. Bioeng., XV:603–606 (1973)], the enzyme may be selectively recovered from media, including media containing suspended solids, allowing recycling in enzyme reactors. When used as solid supports in immunoassays or other competitive binding assays, magnetic particles permit homogeneous reaction conditions (which promote optimal binding kinetics and minimally alter analyte-adsorbent equilibrium) and facilitate separation of bound from unbound analyte, compared to centrifugation. Centrifugal separations are time-consuming, require expensive and energy-consuming equipment and pose radiological, biological and physical hazards. Magnetic separations, on the other hand, are relatively rapid and easy, requiring simple equipment. Finally, the use of non porous adsorbent-coupled magnetic particles in affinity chromatography systems allows better mass transfer and results in less fouling than in conventional affinity chromatography systems.

Although the general concept of magnetizing molecules by coupling them to magnetic particles has been discussed and the potential advantages of using such particles for biological purposes recognized, the practical development of magnetic separations has been hindered by several critical properties of magnetic particles developed thus far.

Large magnetic particles (mean diameter in solution greater than 10 microns($\mu$)) can respond to weak magnetic fields and magnetic field gradients; however, they tend to settle rapidly, limiting their usefulness for reactions requiring homogeneous conditions. Large particles also have a more limited surface area per weight than smaller particles, so that less material can be coupled to them. Examples of large particles are those of Robinson et al. [supra] which are 50–125$\mu$ in diameter, those of Mosbach and Anderson [Nature, 270:259–261 (1977)] which are 60–140$\mu$ in diameter and those of Guesdon et al. [J. Allergy Clin. Immunol. 61(1):23–27 (1978)] which are 50–160$\mu$ in diameter. Composite particles made by Hersh and Yaverbaum [U.S. Pat. No. 3,933,997] comprise ferromagnetic iron oxide ($Fe_3O_4$) carrier particles. The iron oxide carrier particles were reported to have diameters between 1.5 and 10$\mu$. However, based on the reported settling rate of 5 minutes and coupling capacity of only 12 mg of protein per gram of composite particles [L. S. Hersh and S. Yaverbaum, Clin. Chim. Acta, 63:69–72 (1975)], the actual size of the composite particles in solution is expected to be substantially greater than 10$\mu$.

The Hersh and Yaverbaum ferromagnetic carrier particles of U.S. Pat. No. 3,933,997 are silanized with silanes capable of reacting with anti-digoxin antibodies to chemically couple the antibodies to the carrier particles. Various silane couplings are discussed in U.S. Pat. No. 3,652,761, which is hereby incorporated by reference. That the diameters of the composite particles are probably greater than 10$\mu$ may be explained, at least in part, by the method of silanization employed in the Hersch and Yaverbaum patent. Procedures for silanization known in the art generally differ from each other in the media chosen for the polymerization of silane and its deposition on reactive surfaces. Organic solvents such as toluene [H. W. Weetall, in: Methods in Enzymology, K. Mosbach (ed.), 44:134–148, 140 (1976)], methanol [U.S. Pat. No. 3,933,997] and chloroform [U.S. Pat. No. 3,652,761] have been used. Silane depositions from aqueous alcohol and aqueous solutions with acid [H. W. Weetall, in: Methods in Enzymology, supra, p. 139 (1976)] have also been used. Each of these silanization procedures employs air and/or oven drying in a dehydration step. When applied to silanization of magnetic carrier particles such dehydration methods allow the silanized surfaces of the carrier particles to contact each other, potentially resulting in interparticle bonding, including, e.g., cross linking between particles by siloxane formation, van der Waals interactions or physical adhesion between adjacent particles. This interparticle bonding yields covalently or physically bonded aggregates of silanized carrier particles of considerably larger diameter than individual carrier particles. Such aggregates have low surface area per unit weight and hence, a low capacity for coupling with molecules such as antibodies, antigens or enzymes. Such aggregates also have gravitational settling times which are too short for many applications.

Small magnetic particles with a mean diameter in solution less than about 0.03$\mu$ can be kept in solution by thermal agitation and therefore do not spontaneously settle. However, the magnetic field and magnetic field gradient required to remove such particles from solution are so large as to require heavy and bulky magnets for their generation, which are inconvenient to use in bench top work. Magnets capable of generating magnetic fields in excess of 5000 Oersteds are typically required to separate magnetic particles of less than 0.03$\mu$ in diameter. An approximate quantitative relationship between the net force (F) acting on a particle and the magnetic field is given by the equation below (Hirschbein et al., supra):

$$F=(X_v-X_v°)VH(dH/dx),$$

where $X_v$ and $X_v°$ are the volume susceptibilities of the particle and the medium, respectively, V is the volume of the particle, H is the applied magnetic field and dH/ox is the magnetic field gradient. This expression is only an approximation because it ignores particle shape and particle interactions. Nevertheless, it does indicate that the force on a magnetic particle is directly proportional to the volume of the particle.

Magnetic particles of less than 0.03$\mu$ are used in so-called ferrofluids, which are described, for example, in U.S. Pat. No. 3,531,413. Ferrofluids have numerous applications, but are impractical for applications requiring separation of the magnetic particles from surrounding media because of the large magnetic fields and magnetic field gradients required to effect the separations.

Ferromagnetic materials in general become permanently magnetized in reponse to magnetic fields. Materials termed "superparamagnetic" experience a force in a magnetic field gradient, but do not become permanently magnetized. Crystals of magnetic iron oxides may be either ferromagnetic or superparamagnetic, depending on the size of the crystals. Superparamagnetic oxides of iron generally result when the crystal is less than about 300 Å(0.03$\mu$) in diameter; larger crystals generally have a ferromagnetic character. Following initial exposure to a magnetic field, ferromagnetic particles tend to aggregate because of magnetic attraction between the permanently magnetized particles, as has been noted by Robinson et al. [supra] and by Hersh and Yaverbaum [supra].

Dispersible magnetic iron oxide particles reportedly having 300 A diameters and surface amine groups were prepared by base precipitation of ferrous chloride and ferric chloride ($Fe^{2+}/Fe^{3+}=1$) in the presence of polyethylene imine, according to Rembaum in U.S. Pat. No. 4,267,234. Reportedly, these particles were exposed to a magnetic field three times during preparation and were described as redispersible. The magnetic particles were mixed with a glutaraldehyde suspension polymerization system to form magnetic polyglutaraldehyde microspheres with reported diameters of 0.1$\mu$. Polyglutaraldehyde microspheres have conjugated aldehyde groups on the surface which can form bonds to amino containing molecules such as proteins. However, in general, only compounds which are capable of reacting with aldehyde groups can be directly linked to the surface of polyglutaraldehyde microspheres. Moreover, magnetic polyglutaraldehyde microspheres are not sufficiently stable for certain applications.

2.2. Separations in Radioimmunoassays

Radioimmunoassay (RIA) is a term used to describe methods for analyzing the concentrations of substances involving a radioactively labeled substance which binds to an antibody. The amount of radioactivity bound is altered by the presence of an unlabeled test substance capable of binding to the same antibody. The unlabeled substance, if present, competes for binding sites with the labeled substance and thus decreases the amount of radioactivity bound to the antibody. The decrease in bound radioactivity can be correlated to the concentration of the unlabeled test substance by means of a standard curve. An essential step of RIA is the separation of bound and free label which must be accomplished in order to quantitate the bound fraction.

A variety of conventional separation approaches have been applied to radioimmunoassays (RIA) including coated tubes, particulate systems, and double antibody separation methods. Coated tubes, such as described in U.S. Pat. No. 3,646,346, allow separation of bound and free label without centrifugation but suffer from two major disadvantages. First, the surface of the tube limits the amount of antibody that can be employed in the reaction. Second the antibody is far removed (as much as 0.5 cm) from some antigen, slowing the reaction between the antibody and antigen [G. M. Parsons, in: Methods in Enzymology, J. Langone (ed.) 73:225 (1981); and P. N. Nayak, The Ligand Quarterly 4(4):34 (1981)].

Antibodies have been attached to particulate systems to facilitate separation [see, e.g., U.S. Pat. Nos. 3,652,761 and 3,555,143]. Such systems have large surface areas permitting nearly unlimited amounts of antibody to be used, but the particulates frequently settle during the assay. The tube frequently must be agitated to achieve even partial homogeneity [P. M. Jacobs, The Ligand Quarterly, 4(4):23–33 (1981)]. Centrifugation is still required to effect complete separation of bound and free label.

Antibodies may react with labeled and unlabeled molecules followed by separation using a second antibody raised to the first antibody [Id.]. The technique, termed the double antibody method, achieves homogeneity of antibody during reaction with label but requires an incubation period for reaction of first and second antibodies followed by a centrifugation to pellet the antibodies.

Antibodies have been attached to magnetic supports in an effort to eliminate the centrifugation steps in radioimmunoassays for nortriptyline, methotrexate, digoxin, thyroxine and human placental lactogen [R. S. Kamel et al., Clin. Chem., 25(12):1997–2002 (1979); R. S. Kamel and J. Gardner, Clin. Chim. Acta, 89:363–370 (1978); U.S. Pat. No. 3,933,997; C. Dawes and J. Gardner, Clin. Chim. Acta, 86:353–356 (1978); D. S. Ithakissios et al., Clin. Chim. Acta, 84:69–84 (1978); D. S. Ithakissios and D. O. Kubiatowicz, Clin. Chem. 23(11):2072–2079 (1977); and L. Nye et al., Clin. Chim. Acta, 69:387–396 (1976), repectively, hereby incorporated by reference]. Such methods suffer from large particle sizes (10–100μ in diameter) and require agitation to keep the antibody dispersed during the assay. Since substantial separation occurs from spontaneous settling in the absence of a magnetic field these previous methods are in fact only magnetically assisted gravimetric separations. The problem of settling was addressed by Davies and Janata whose approach in U.S. Pat. No. 4,177,253 was to employ magnetic particles comprising low density cores of materials such as hollow glass or polyproplyene (4–10μ in diameter) with magnetic coatings (2 mμ10μ thick) covering a proportion of the particle surface. Antiestradiol antibodies were coupled to such particles and their potential usefulness in estradiol RIAs was demonstrated. While this approach may have overcome the problem of settling, the particle size and the magnetic coating nonetheless present limitations on surface area and hence limitations on the availability of sites for antibody coupling.

2.3. Application of Magnetic Separations in other Biological Systems

Magnetic separations have been applied in other biological systems besides RIA. Several nonisotopic immunoassays, such as fluoroimmunoassays (FIA) and enzyme-immunoassays (EIA) have been developed which employ antibody-coupled (or antigen-coupled) magnetic particles. The principle of competitive binding is the same in FIA and EIA as in RIA except that fluorophores and enzymes, respectively, are substituted for radioisotopes as label. By way of illustration, M. Pourfarzaneh et al. and R. S. Kamel et al. developed magnetizable solid-phase FIAs for cortisol and phenytoin, respectively, utilizing ferromagnetic cellulose/iron oxide particles to which antibodies were coupled by cyanogen bromide activation [M. Pourfarzaneh et al., Clin. Chem., 26(6):730–733 (1980); R. S. Kamel et al., Clin. Chem., 26(9):1281–1284 (1980)].

A non-competitive solid phase sandwich technique EIA for the measurement of IgE was described by J.- L. Guesdon et al. [J. Allergy Clin. Immunol., 61(1):23–27 (1978)]. By this method, anti-IgE antibodies coupled by glutaraldehyde activation to magnetic polyacrylamideagarose beads are incubated with a test sample containing IgE to allow binding. Bound IgE is quantitated by adding a second anti-IgE antibody labeled with either alkaline phosphatase or $\beta$-galactosidase. The enzyme labeled second antibody complexes with IgE bound to the first antibody, forming the sandwich, and the particles are separated magnetically. Enzyme activity associated with the particles, which is proportional to bound IgE is then measured permitting IgE quantitation.

A magnetizable solid phase non-immune radioassay for vitamin $B_{12}$ has been reported by D. S. Ithakissios and D. O. Kubiatowicz [Clin. Chem. 23(11):2072–2079 (1977)]. The principle of competitive binding in non-immune radioassays is the same as in RIA with both assays employing radioisotopic labels. However, while RIA is based on antibody-antigen binding, non immune radioassays are based on the binding or interaction of certain biomolecules like vitamin $B_{12}$ with specific or non-specific binding, carrier, or receptor proteins. The magnetic particles of Ithakissios and Kubiatowicz were composed of barium ferrite particles embedded in a water-insoluble protein matrix.

In addition to their use in the solid phase biological assays just described, magnetic particles have been used for a variety of other biological purposes. Magnetic particles have been used in cell sorting systems to isolate select viruses, bacteria and other cells from mixed populations [U.S. Pat. Nos. 3,970,518; 4,230,685; and 4,267,234, hereby incorporated by reference]. They have been used in affinity chromatography systems to selectively isolate and purify molecules from solution and are particularly advantageous for purifications from colloidal suspensions [K. Mosbach and L. Anderson, Nature 170:259–261 (1977), hereby incorporated by reference]. Magnetic particles have also been used as the solid phase support in immobilized enzyme systems. Enzymes coupled to magnetic particles are contacted with substrates for a time sufficient to catalyze the biochemical reaction. Thereafter, the enzyme can be magnetically separated from products and unreacted substrate and potentially can be reused. Magnetic particles have been used as supports for $\alpha$-chymotrypsin, $\beta$-galactosidase [U.S. Pat. No. 4,152,210, hereby incorporated by reference] and glucose isomerase [U.S. Pat. No. 4,343,901, hereby incorporated by reference] in immobilized enzyme systems.

3. Nomenclature

The term "magnetically responsive particle" or "magnetic particle" is defined as any particle dispersible or suspendable in aqueous media without significant gravitational settling and separable from suspension by application of a magnetic field, which particle comprises a magnetic metal oxide core generally surrounded by an adsorptively or covalently bound sheath or coat bearing organic functionalities to which bioaffinity adsorbents may be covalently coupled. The term "magnetocluster" is a synonym of "magnetically responsive particle" and "magnetic particle".

The term "metal oxide core" is defined as a crystal or group (or cluster) of crystals of a transition metal oxide having ferrospinel structure and comprising trivalent and divalent cations of the same or different transition metals. By way of illustration, a metal oxide core may be comprised of a cluster of superparamagnetic crystals of an iron oxide, or a cluster of ferromagnetic crystals of an iron oxide, or may consist of a single ferromagnetic crystal of an iron oxide.

The term "bioaffinity adsorbent" is defined as any biological or other organic molecule capable of specific or nonspecific binding or interaction with another biological molecule, which binding or interaction may be referred to as "ligand/ligate" binding or interaction and is exemplified by, but not limited to, antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector or repressor/inducer bindings or interactions.

The term "coupled magnetically responsive particle" or "coupled magnetic particle" is defined as any magnetic particle to which one or more types of bioaffinity adsorbents are coupled by covalent bonds, which covalent bonds may be amide, ester, ether sulfonamide, disulfide, azo or other suitable organic linkages depending on the functionalities available for bonding on both the coat of the magnetic particle and the bioaffinity adsorbent(s).

The term "silane" refers to any bifunctional organosilane and is defined as in U.S. Pat. No. 3,652,761 as an organofunctional and silicon functional silicon compound characterized in that the silicon portion of the molecule has an affinity for inorganic materials while the organic portion of the molecule is tailored to combine with organics. Silanes are suitable coating materials for metal oxide cores by virtue of their silicon-functionalities and can be coupled to bioaffinity adsorbents through their organofunctionalities.

The term "superparamagnetism" is defined as that magnetic behavior exhibited by iron oxides with crystal size less than about 300Å, which behavior is characterized by responsiveness to a magnetic field without resultant permanent magnetization.

The term "ferromagnetism" is defined as that magnetic behavior exhibited by iron oxides with crystal size greater than about 500Å, which behavior is characterized by responsiveness to a magnetic field with resultant permanent magnetization.

The term "ferrofluid" is defined as a liquid comprising a colloidal dispersion of finely divided magnetic particles of subdomain size, usually 50–500 Å, in a carrier liquid and a surfactant material, which particles remain substantially uniformly dispersed throughout the liquid carrier even in the presence of magnetic fields of up to about 5000 Oersteds.

The term "immunoassay" is defined as any method for measuring the concentration or amount of an analyte in a solution based on the immunological binding or interaction of a polyclonal or monoclonal antibody and an antigen, which method (a) requires a separation of bound from unbound analyte; (b) employs a radioisotopic, fluorometric, enzymatic, chemiluminescent or other label as the means for measuring the bound and/or unbound analyte; and (c) may be described as "competitive" if the amount of bound measurable label is generally inversely proportional to the amount of analyte originally in solution or "non-competitive" if the amount of bound measurable label is generally directly proportional to the amount of analyte originally in solution. Label may be in the antigen, the antibody, or in double antibody methods, the second antibody. Immunoassays are exemplified by, but are not limited to, radioimmunoassays (RIA), immunoradiometric assays (IRMA), fluoroimmunoassays (FIA), enzyme immunoassays (EIA), and sandwich method immunoassays.

The term "binding assay" or "non immune assay" is defined as any method for measuring the concentration or amount of an analyte in solution based on the specific or nonspecific binding or interaction, other than antibody/antigen binding or interaction, of a bioaffinity adsorbent and another biological or organic molecule, which method (a) requires a separation of bound from unbound analyte; (b) employs a radioisotopic, fluorometric, enzymatic, chemiluminescent or other label as the means for measuring the bound and/or unbound analyte; and (c) may be described as "competitive" if the amount of bound measurable label is generally inversely proportional to the amount of analyte originally in solution or "non-competitive" if the amount of bound measurable label is generally directly proportional to the amount of analyte originally in solution.

The term "immobilized enzyme reaction" is defined as any enzymatically catalyzed biochemical conversion or synthesis or degradation wherein the enzyme molecule or active site thereof is not freely soluble but is adsorptively or covalently bound to a solid phase support, which support is suspended in or contacted with the surrounding medium and which may be reclaimed or separated from said medium.

The term "affinity chromatography" is defined as a method for separating, isolating, and/or purifying a selected molecule from its surrounding medium on the basis of its binding or interaction with a bioaffinity adsorbent adsorptively or covalently bound to a solid phase support, which support is suspended in or contacted with the surrounding medium and which may be reclaimed or separated from said medium.

4. SUMMARY OF THE INVENTION

This invention provides novel magnetic particles useful in biological applications involving the separation of molecules from or the directed movement of molecules in the surrounding medium. Methods and compositions for preparing and using the magnetic particles are provided.

The magnetic particles comprise a magnetic metal oxide core generally surrounded by an adsorptively or covalently bound silane coat to which a wide variety of bioaffinity adsorbents can be covalently bonded through selected coupling chemistries. The magnetic metal oxide core preferably includes a group of superparamagnetic iron-oxide crystals, the coat is preferably a silane polymer and the coupling chemistries include, but are not limited to, diazotization, carbodiimide and glutaraldehyde couplings.

The magnetic particles produced by the method described herein can remain dispersed in an aqueous medium for a time sufficient to permit the particles to be used in a number of assay procedures. The particles are preferably between about 0.1 and about 1.5μ in diameter. Remarkably, preferred particles of the invention with mean diameters in this range can be produced with a surface area as high as about 100 to 150 m$_2$/gm, which provides a high capacity for bioaffinity adsorbent coupling. Magnetic particles of this size range overcome the rapid settling problems of larger particles, but obviate the need for large magnets to generate the magnetic fields and magnetic field gradients required to separate smaller particles. Magnets used to effect separations of the magnetic particles of this invention need only generate magnetic fields between about 100 and about 1000 Oersteds. Such fields can be obtained with permanent magnets which are preferably smaller than the container which holds the dispersion of magnetic particles and thus, may be suitable for benchtop use. Although ferromagnetic particles may be useful in certain applications of the invention, particles with superparamagnetic behavior are usually preferred since superparamagnetic particles do not exhibit the magnetic aggregation associated with ferromagnetic particles and permit redispersion and reuse.

The method for preparing the magnetic particles may comprise precipitating metal salts in base to form fine magnetic metal oxide crystals, redispersing and washing the crystals in water and in an electrolyte. Magnetic separations may be used to collect the crystals between washes if the crystals are superparamagnetic. The crystals may then be coated with a material capable of adsorptively or covalently bonding to the metal oxide and bearing organic functionalities for coupling with bioaffinity adsorbents.

In one embodiment the coating around the metal oxide core is a polymer of silane. The silanization may be performed by redispersing the magnetic metal oxide crystals in an acidic organic solution, adding an organosilane, dehydrating by heating in the presence of a wetting agent miscible both in water and the organic solution, and washing the resulting magnetic silanized metal oxides. Alternatively, silanization may be performed in acidic aqueous solution.

The magnetic particles of this invention can be covalently bonded by conventional coupling chemistries to bioaffinity adsorbents including, but not limited to, antibodies, antigens and specific binding proteins, which coupled magnetic particles can be used in immunoassays or other binding assays for the measurement of analytes in solution. Such assays preferably comprise mixing a sample containing an unknown concentration of analyte with a known amount of labeled analyte in the presence of magnetic particles coupled to a bioaffinity adsorbent capable of binding to or interacting with both unlabeled and labeled analyte, allowing the binding or interaction to occur, magnetically separating the particles, measuring the amount of label associated with the magnetic particles and/or the amount of label free in solution and correlating the amount of label to a standard curve constructed similarly to determine the concentration of analyte in the sample.

The magnetic particles of this invention are suitable for use in immobilized enzyme systems, particularly where enzyme recycling is desired. Enzymatic reactions are preferably carried out by dispersing enzyme-coupled magnetic particles in a reaction mixture containing substrate(s), allowing the enzymatic reaction to occur, magnetically separating the enzyme-coupled magnetic particle from the reaction mixture containing product(s) and unreacted substrate(s) and, if desired, redispersing the particles in fresh substrate(s) thereby reusing enzyme.

Affinity chromatography separations and cell sorting can be performed using the magnetic particles of this invention, preferably by dispersing bioaffinity adsorbent-coupled magnetic particles in solutions or suspensions containing molecules or cells to be isolated and/or purified, allowing the bioaffinity adsorbent and the desired molecules or cells to interact, magnetically separating the particles from the solutions or suspension and recovering the isolated molecules or cells from the magnetic particles.

It is further contemplated that the magnetic particles of this invention can be used in in vivo systems for the diagnostic localization of cells or tissues recognized by the particular bioaffinity adsorbent coupled to the particle and also for magnetically directed delivery of therapeutic agents coupled to the particles to pathological sites.

The magnetic particles of this invention overcome problems associated with the size, surface area, gravitational settling rate and magnetic character of previously developed magnetic particles. Gravitational settling times in excess of about 1.5 hours can be achieved with magnetic particles of the invention, where the gravitational settling time is defined to be the time for the turbidity of a dispersion of particles of the invention in the absence of a magnetic field to fall by fifty percent. Magnetic separation times of less than about ten minutes can be achieved with magnetic particles of the invention by contacting a vessel containing a dispersion of the particles with a pole face of a permanent magnet no larger in volume than the volume of the vessel, where the magnetic separation time is defined to be the time for the turbidity of the dispersion to fall by 95 percent. Furthermore, the use of silane as the coating surrounding the metal oxide core of the magnetic particles described herein makes possible the coupling of a wide variety of molecules under an equally wide variety of coupling conditions compared to other magnetic particle coatings known in the art with more limited coupling functionalities.

Preferred magnetically responsive particles of the invention have metal oxide cores comprised of clusters of superparamagnetic crystals, affording efficient separation of the particles in low magnetic fields (100-1000 Oersteds) while maintaining superparamagnetic properties. Aggregation of particles is controlled during particle synthesis to produce particles which are preferably small enough to avoid substantial gravitational settling over times sufficient to permit dispersions of the particles to be used in an intended biological assay or other application. The advantage of having superparamagnetic cores in magnetically responsive particles is that such particles can be repeatedly exposed to magnetic fields. Because they do not become permanently magnetized and therefore do not magnetically aggregate, the particles can be redispersed and reused. Even after silanization, preferred particles of the invention having cores made up of clusters of crystals exhibit a remarkably high surface area per unit weight and a generally correspondingly high coupling capacity, which indicates that such particles have an open or porous structure.

None of the prior art magnetic particles used in the biological systems described in Section 2 above have the same composition, size, surface area, coupling versatility, settling properties and magnetic behavior as the magnetic particles of the invention. The magnetic particles of this invention are suitable for many of the assays, enzyme immobilization, cell sorting and affinity chromatography procedures reported in the literature and, in fact, overcome many of the problems associated with particle settling and reuse experienced in the past with such procedures.

5. BRIEF DESCRIPTION OF THE FIGURES

6. DETAILED DESCRIPTION OF THE INVENTION

6.1. Magnetic Particle Preparation

Figure 1:
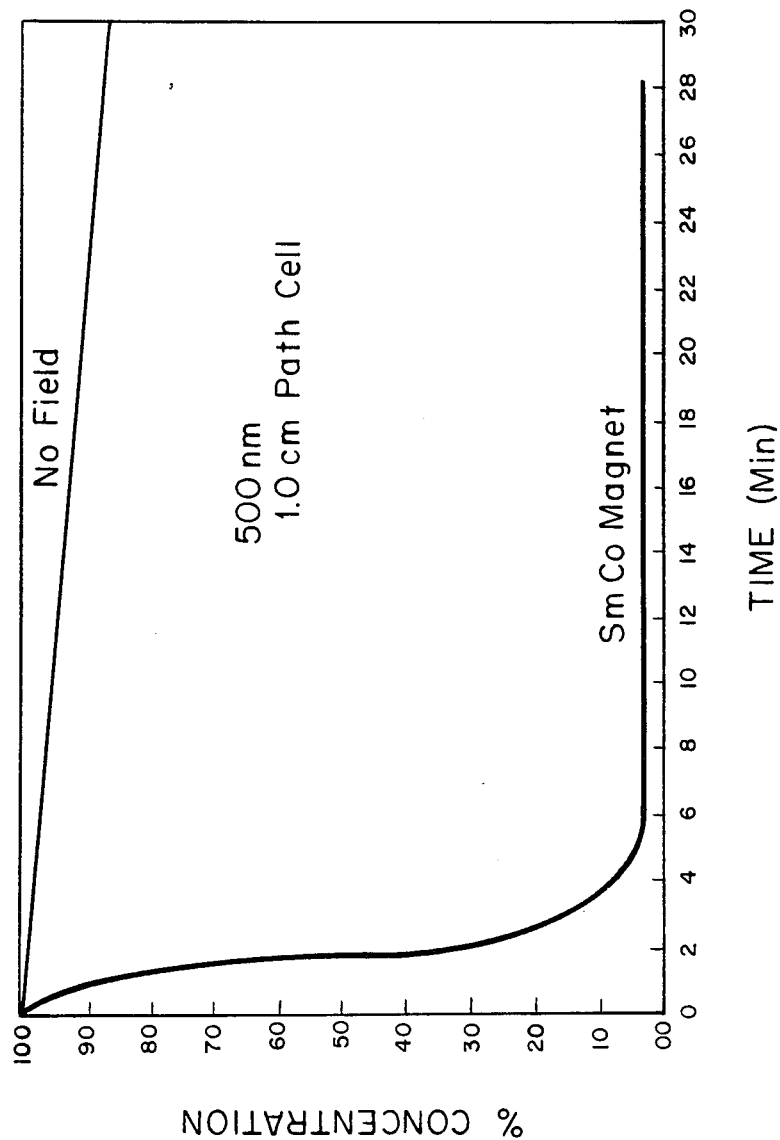
FIG. 1 is a graphical representation of the change in turbidity (% concentration) of a suspension of magnetic particles in the presence and absence of a magnetic field as a function of time.

Preferred magnetic particles of the invention may be made in two steps. First, superparamagnetic iron oxides are made by precipitation of divalent ($Fe^{2+}$) and trivalent ($Fe^{3+}$) iron salts, e.g., $FeCl_2$ and $FeCl_3$, in base. Secondly an organosilane coating is applied to the iron oxide.

The ratio of $Fe^{2+}$ and $Fe^{3+}$ can be varied without substantial changes in the final product by increasing the amount of $Fe^{2+}$ while maintaining a constant molar amount of iron. The preferred $Fe^{2+}/Fe^{3+}$ ratio is 2/1 but an $Fe^{2+}/Fe^{3+}$ ratio of 4/1 also works satisfactorily in the procedure of Section 7.1 (See also Section 7.7). An $Fe^{2+}/Fe^{3+}$ ratio of ½ produces magnetic particles of slightly inferior quality to those resulting from the higher $Fe^{2+}/Fe^{3+}$ ratios This magnetic oxide tends to "bleed" or become soluble during the rinsing procedure of Section 7.1 and the particle size is more heterogeneous than the resulting from $Fe^{2+}/Fe^{3+}$ of 2/1 or 4/1. Nevertheless, it can be silanized to yield a usable magnetic particle as demonstrated in Section 7.7.

Aqueous solutions of the iron salts are mixed in a base such as sodium hydroxide which results in the formation of a crystalline precipitate of superparamagnetic iron oxide. The precipitate is washed repeatedly with water by magnetically separating it and redispersing it until a neutral pH is reached. The precipitate is then washed once in an electrolytic solution, e.g. a sodium chloride solution. The electrolyte wash step is important to insure fineness of the iron oxide crystals. Finally the precipitate is washed with methanol until a residue of 1.0% (V/V) water is left.

The repeated use of magnetic fields to separate the iron oxide from suspension during the washing steps is facilitated by superparamagnetism. Regardless of how many times the particles are subjected to magnetic fields, they never become permanently magnetized and consequently can be redispersed by mild agitation. Permanently magnetized (ferromagnetic) metal oxides cannot be prepared by this washing procedure as they tend to magnetically aggregate after exposure to magnetic fields and cannot be homogeneously redispersed.

Other divalent transition metal salts such as magnesium, manganese, cobalt, nickel, zinc and copper salts may be substituted for iron (II) salts in the precipitation procedure to yield magnetic metal oxides. For example, the substitution of divalent cobalt chloride ($CoCl_2$) for $FeCl_2$ in the procedure of Section 7.1 produced ferromagnetic metal oxide particles. Ferromagnetic metal oxides such as that produced with $CoCl_2$, may be washed in the absence of magnetic fields by employing conventional techniques of centrifugation or filtration between washings to avoid magnetizing the particles. As long as the resulting ferromagnetic metal oxides are of sufficiently small diameter to remain dispersed in aqueous media, they may also be silanized and coupled to bioaffinity adsorbents for use in systems requiring a single magnetic separation, e.g. certain radioimmunoassays. Ferromagnetism limits particle usefulness in those applications requiring redispersion or reuse.

Magnetic metal oxides produced by base precipitation may be coated by any one of several suitable silanes. The silane coupling materials have two features: They are able to adsorptively or covalently bind to the metal oxide and are able to form covalent bonds with bioaffinity adsorbents through organofunctionalities.

When silanization is used to coat the metal oxide cores of the magnetic particles of this invention, organosilanes of the general formula $R-Si(OX)_3$ may be used wherein $(OX)_3$ represents a trialkoxy group, typically trimethoxy or triethoxy, and R represents any aryl or alkyl or aralkyl group terminating in aminophenyl, amino, hydroxyl, sulphydryl, aliphatic, hydrophobic or mixed function (amphipathic) or other organic group suitable for covalent coupling to a bioaffinity adsorbent. Such organosilanes include, but are not limited to, p-aminophenyltrimethoxysilane, 3-aminopropyltrimethoxysilane, N-2-aminoethy-3-aminopropyltrimethoxysilane, triaminofunctional silane ($H_2NCH_2CH_2$—NH—$CH_2CH_2$—NH—$CH_2CH_2$—$CH_2$—Si—$(OCH_3)_3$, n-dodecyltriethoxysilane and n-hexyltrimethoxysilane. [For other possible silane coupling agents see U.S. Pat. No. 3,652,761, incorporated by reference, supra]. Generally, chlorosilanes cannot be employed unless provision is made to neutralize the hydrochloric acid evolved.

In one embodiment, the silane is deposited on the metal oxide core from acidic organic solution. The silanization reaction occurs in two steps. First, a trimethoxysilane is placed in an organic solvent, such as methanol, water and an acid, e.g., phosphorous acid or glacial acetic acid. It condenses to form silane polymers;

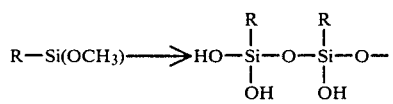

Secondly, these polymers associate with the metal oxide, perhaps by forming a covalent bond with surface OH groups through dehydration:

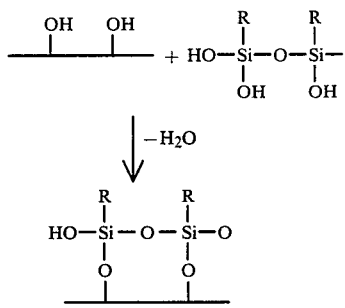

Adsorption of silane polymers to the metal oxide is also possible.

An important aspect of the acidic organic silanization procedure of this invention is the method of dehydration used to effect the adsorptive or covalent binding of the silane polymer to the metal oxide. This association is accomplished by heating the silane polymer and metal oxide in the presence of a wetting agent miscible in both the organic solvent and water. Glycerol, with a boiling of about 290° C., is a suitable wetting agent. Heating to about 160°–170° in the presence of glycerol serves two purposes. It insures the evaporation of water, the organic solvent (which may be e.g., methanol, ethanol, dioxane, acetone or other moderately polar solvents) and any excess silane monomer. Moreover, the presence of glycerol prevents the aggregation or clumping and potential cross linking, of particles that is an inherent problem of other silanization techniques known in the art wherein dehydration is brought about by heating to dryness.

In another embodiment an acidic aqueous silanization procedure is used to deposit a silane polymer on surface of the metal oxide core. Here, the metal oxide is suspended in an acidic (pH approximately 4.5) solution of 10% silane monomer. Silanization is achieved by heating for about two hours at 90°–95° C. Glycerol dehydration is again used.

The presence of silane on iron oxide particles was confirmed by the following observations. First, after treatment with 6N hydrochloric acid, the iron oxide was dissolved and a white, amorphous residue was left which is not present if unsilanized iron oxide is similarly digested. The acid insoluble residue was silane. Secondly, the diazotization method of Section 7.4 permits the attachment of antibodies to the particles. Diazotization does not promote the attachment of unsilanized particles. Finally, the attachment of antibody is extremely stable, far more stable than that resulting from the adsorption of antibodies to metal oxides.

6.2. Silane Coupling Chemistry

An initial consideration for choosing a silane coating and the appropriate chemistry for coupling bioaffinity adsorbents to magnetic particles is the nature of the bioaffinity adsorbent itself, its susceptibilities to such factors as pH and temperature as well as the availability of reactive groups on the molecule for coupling. For instance, if an antibody is to be coupled to the magnetic particle, the coupling chemistry should be nondestructive to the immunoglobulin protein, the covalent linkage should be formed at a site on the protein molecule such that the antibody/antigen interaction will not be blocked or hindered, and the resulting linkage should be stable under the coupling conditions chosen. Similarly, if an enzyme is to be coupled to the magnetic particle, the coupling chemistry should not denature the enzyme protein and the covalent linkage should be formed at a site on the molecule other than the active or catalytic site or other sites that may interfere with enzyme/substrate or enzyme/cofactor interactions.

A variety of coupling chemistries are known in the art and have been described in U.S. Pat. No. 3,652,761 incorporated by reference, supra. By way of illustration, diazotization can be used to couple p-aminophenyl-terminated silanes to immunoglobulins. Coupling of immunoglobulins and other proteins to 3-aminopropyl-terminted and N-2-aminoethyl3-aminopropyl-terminated silanes has been accomplished by the use of glutaraldehyde. The procedure consists of two basic steps: (1) activation of the particle by reaction with glutaraldehyde followed by removal of unreacted glutaraldehyde and (2) reaction of the proteins with the activated particles followed by removal of the unreacted proteins. The procedure is widely used for the immobilization of proteins and cells [A. M. Klibanov, Science, 219:722 (1983), hereby incorporated by reference]. If the magnetic particles are coated by carboxyterminated silanes, bioaffinity adsorbents such as proteins and immunoglobulins can be coupled to them by first treating the particles with 3-(3-dimethylaminopropyl) carbodiimide.

Generally, magnetic particles coated with silanes bearing certain organofunctionalities can be modified to substitute more desirable functionalities for those already present on the surface. For example, diazo derivatives can be prepared from 3-aminopropyltriethoxysilane by reaction with p-nitro-benzoic acid, reduction of the nitro group to an amine and then diazotiation with nitrous acid. The same silane can be converted to the isothiocyanoalkylsilane derivative by reaction of the amino-function group with thiophosgene.

To effect coupling to the magnetic particle, an aqueous solution of a bioaffinity adsorbent can be contacted with the silane coated particle at or below room temperature. When a protein (or immunoglobulin) is to be coupled, generally a ratio of 1:10–1:30, mg protein: mg particle is used. Contact periods of between about 3 to 24 hours are usually sufficient for coupling. During this period, the pH is maintained at a value that will not denature the bioaffinity adsorbent and which best suits the type of linkage being formed, e.g. for azo linkages, a pH of 8–9.

It has been observed that after coupling of antibodies to silane coated magnetic particles by either the diazotization, carbodiimide, or glutaraldehyde methods described in greater detail in Section 7.5, 7.8 and 7.10, respectively, the antibodies remain magnetic even after the following rigorous treatments: 24 hours at 50° C. in phosphate buffered saline (PBS), 21 days at 37° C. in PBS, 30 minutes at 23° C. in 1M sodium chloride, and repeated rinses in ethanol or methanol at room temperature. Antibodies adsorbed to iron oxides are substantially detached by any of these treatments. These results indicate that the silane is very tightly associated with the metal oxide and that the coupling of antibody to the particle results from an essentially irreversible covalent coupling. The tight association of the silane to the metal oxide together with the covalent coupling of bioaffinity adsorbents (e.g., antibodies) are features which impart stability onto coupled magnetic particles, a commercially important attribute.

6.3. Use of Magnetic Particles in Biological Assays

The magnetic particles of this invention may be used in immunoassays and other binding assays as defined in Section 3. The most prevalent types of assays used for diagnostic and research purposes are radioimmunoassays, fluoroimmunoassays, enzyme-immunoassays, and non-immune radioassays, based on the principle of competitive binding. Basically, a ligand, such as an antibody or specific binding protein, directed against a ligate, such as an antigen, is saturated with an excess of labeled ligate (*ligate). [Alternatively, competitive assays may be run with labeled ligand and unlabeled ligate. Non-competitive assays, so-called sandwich assays, are also widely employed.] By the method of this invention, the ligand is coupled to a magnetic particle. Examples of labels are radioisotopes: tritium, $^{14}$-carbon, $^{57}$-cobalt and, preferably, $^{125}$-iodine; fluorometric labels: rhodamine or fluorescein isothiocyanate; and enzymes (generally chosen for the ease with which the enzymatic reaction can be measured): alkaline phosphatase or $\beta$-D-galactosidase. If nonlabeled ligate is added to ligand along with *ligate, less *ligate will be found in the ligand-ligate complex as the ratio of unlabeled to labeled ligate increases. If the ligand-*ligate complex can be physically separated from *ligate, the amount of unlabeled ligate in a test substance can be determined.

To measure unlabeled ligate, a standard curve must be constructed. This is done by mixing a fixed amount of ligand and *ligate and adding a known amount of unlabeled ligate to each. When the reaction is complete, the ligand-*ligate is separated from *ligate. A graph is then made that relates the label in the collected ligand-*ligate complex to the amount of added unlabeled ligate. To determine the amount of unlabeled ligate in an experimental sample, an aliquot of the sample is added to the same ligand-*ligate mixture used to obtain the standard curve. The ligand-*ligate complex is collected and the label measured, and the amount of unlabeled ligand is read from the standard curve. This is possible with any sample, no matter how complex, as long as nothing interferes with the ligand-*ligate interaction. By the method of this invention, the ligand-*ligate complex is separated magnetically from free *ligate.

This general methodology can be applied in assays for the measurement of a wide variety of compounds including hormones, pharmacologic agents, vitamins and cofactors, hematological substances, virus antigens, nucleic acids, nucleotides, glycosides and sugars. By way of illustration, the compounds listed in Table I are all measurable by magnetic particles immunoassays and binding assays [see D. Freifelder, Physical Biochemistry: Applications to Biochemistry and Molecular Biology, p. 259, W.H. Freeman and Company, San Francisco (1976)].

TABLE I
SUBSTANCES MEASURABLE IN MAGNETIC PARTICLE ASSAYS

Hormones:
Thyroid hormones (thyroxine, triiodothyronine, thyroid binding globulin, thyroid-stimulating hormone, thyroglobulin)
Gastrointestinal hormones (glucagon, gastrin, enteroglucagon, secretin, pancreozymin, vasoactive intestinal peptide, gastric inhibitory peptide, motilin, insulin)
Follicle-stimulating hormone
Leutenizing Hormone
Progesterone
Testosterone
Estriol
Estradiol Prolactin
Thyrocalcitonin
Parathyroid hormone
Human chorionic gonadotrophin
Human placental lactogen
Posterior pituitary peptides (oxytocin, vasopressin, neurophysin)
Bradykinin
Cortisol
Corticotrophin
Human growth hormone Pharmacologic agents:
Digoxin
Theophylline
Morphine and opiate alkaloids
Cardiac glycosides
Prostaglandins
Lysergic acid and derivatives Tetrahydrocannabinol
Barbiturates
Nicotine and metabolic products
Phenothiazines
Amphetamines Vitamins and cofactors:
D, B12, folic acid, cyclic AMP Hematological substances:
Fibrinogen, fibrin, and fibrinopeptides
Plasminogen and plasmin
Antihemophilic factor Prothrombin
Transferrin and ferritin
Erthropoietin Virus antigens:
Hepatitis antigen
Herpes simplex
Vaccinia
Several Groups A arboviruses Polio
Rabies
Q fever
Psittacosis group Nucleic acids and nucleotides:
DNA, RNA, cytosine derivatives

6.4 Use of Magnetic Particles in Immobilized Enzyme Systems

Enzymes may be coupled to the magnetic particles of this invention by the methods described in Section 6.2. They may be used in immobilized enzyme systems, particulary in batch reactors or continuous-flow stirred-tank reactors (CSTR), to facilitate separation of enzyme from product after the reaction has occurred and to permit enzyme reuse and recycle. A method for using enzyme-coupled magnetic particles in biochemical reactions was described by Dunnill and Lilly in U.S. Pat. No. 4,152,210, incorporated by reference, supra. The magnetic particles of this invention may be advantageously substituted for those of Dunnill and Lilly to avoid problems of settling and to allow enzyme recycle. Briefly, substrates are contacted with enzyme-coupled magnetic particles in a reactor under conditions of pH, temperature and substrate concentration that best promote the reaction. After completion of the reaction the particles are magnetically separated from the bulk liquid (which may be a solution or suspension) from which product can be retrieved free of enzyme. The enzyme-coupled magnetic particles can then be reused. Immobilized enzymes (coupled to non-magnetic supports) have been used in a number of industrially important enzymatic reactions, some of which are listed in Table II. The magnetic particles of this invention can be substituted for the non-magnetic solid phases previously employed which include glass, ceramics, polyacrylamide, DEAE-cellulose, chitin, porous silica, cellulose beads and alumino-silicates.

TABLE II
INDUSTRIALLY IMPORTANT IMMOBILIZED ENZYME REACTIONS

| Enzyme | Reactant/Product |
| --- | --- |
| Amylo-glucosidase | Maltose/Glucose |
| Glucose Oxidase | Glucose/gluconic acid |
| Glucoamylase | Starch/glucose, Dextrin/glucose |
| β-Amylase | Starch/maltose |
| Invertase | Sucrose/glucose |
| Glucose isomerase | Glucose/fructose |
| Lactase | Lactose/glucose |
| Trypsin | Proteins/amino acids |
| Aminoacylase | N—acetyl-DL-methionine/methionine |
| Lysozyme | Lysis of *M. lysodeikticus* |

6.5. Use of Magnetic Particles in Affinity Chromatography

The process of affinity chromatography enables the efficient isolation of molecules by making use of features unique to the molecule: the ability to recognize or be recognized with a high degree of selectivity by a bioaffinity adsorbent such as an enzyme or antibody and the ability to bind or adsorb thereto. The process of affinity chromatography simply involves placing a selective bioaffinity adsorbent or ligand in contact with a solution containing several kinds of substances including the desired species, the ligate. The ligate is selectively adsorbed to the ligand, which is coupled to an insoluble support or matrix. The nonbinding species are removed by washing. The ligate is then recovered by eluting with a specific desorbing agent, e.g. a buffer at a pH or ionic strength that will cause detachment of the adsorbed ligate.

By the method of this invention, magnetic particles may be used as the insoluble support to which the ligand is coupled. The particles may be suspended in batch reactors containing the ligate to be isolated. The particles with bound ligate may be separated magnetically from the bulk fluid and washed, with magnetic separations between washes. Finally, the ligate can be recovered from the particle by desorption. The magnetic particles of this invention may be used in a variety of affinity systems exemplified by those listed in Table III.

TABLE III
AFFINITY SYSTEMS

| Ligand, immobile entity | Ligate, soluble entity |
| --- | --- |
| Inhibitor, cofactor, prosthetic group, polymeric substrate | Enzymes; apoenzymes |
| Enzyme | Polymeric inhibitors |
| Nucleic acid, single strand | Nucleic acid, complementary strand |
| Hapten; antigen | Antibody |
| Antibody (IgG) | Proteins; polysaccharides |
| Monosaccharide; polysaccharide | Lectins; receptors |
| Lectin | Glycoproteins; receptors |
| Small target compounds | Binding Proteins |
| Binding Protein | Small target compounds |

7. EXAMPLES

7.1. Preparation of Metal Oxide

The metal oxide particles were prepared by mixing a solution of iron(II) ($Fe^{2+}$) and iron(III) ($Fe^{3+}$) salts with base as follows: a solution that is 0.5 M ferrous chloride ($FeCl_2$) and 0.25 M ferric chloride ($FeCl_3$) (200 mls) was mixed with 5 M sodium hydroxide (NaOH) (200 mls) at 60° C. by pouring both solutions into a 500 ml beaker container 100 mls of distilled water. All steps were performed at room temperature unless otherwise indicated. The mixture was stirred for 2 minutes during which time a black, magnetic precipitate formed. After settling, the volume of the settled precipitate was approximately 175 mls. The concentration of iron oxide in the precipitate was about 60 mg/ml (based on a yield of 11.2 gms of iron oxide as determined infra). This is in contrast to commercially available magnetic iron oxides, such as Pfizer #2228 $\gamma Fe_2O_3$ (Pfizer Minerals, Pigments and Metals Division, New York, NY), the standard magnetic oxide for recording tapes, which can attain concentrations of about 700 mg/ml in aqueous slurry. The comparison is included to emphasize the fineness of the particles made by this method. Very fine particles are incapable of dense packing and entrain the most water. Larger and denser particles, on the other hand, pack densely, excluding the most water.

The precipitate was then washed with water until a pH of 6–8 was reached as determined by pH paper. The following washing technique was employed: The particles were suspended in 1.8 liters of water in a 2 liter beaker and collected by magnetic extraction. The beaker was placed on top of a ring magnet, ½ inch high and 6 inches in diameter, which caused the magnetic particles to settle. The water was poured off without the loss of particles by holding the magnet to the bottom of the beaker while decanting. A similar washing technique was employed for all washes throughout, except that volumes were adjusted as necessary. Typically, three washes were sufficient to achieve neutral pH. The magnetic oxide was then washed once with 1.0 liter of 0.02 M sodium chloride (NaCl) in the same beaker.

The water was then replaced with methanol, leaving a trace of water to catalyze hydrolysis of the methoxy silane (see Section 7.2.). This was accomplished by aspirating 800 mls of 0.2 M NaCl and bringing the total volume to 1 liter with methanol. The material was resuspended, and magnetically extracted; 800 mls of supernatant were removed, and another 800 mls of methanol were added. After three additions of methanol, the oxide was ready for silanization in a solution which was approximately 1% (V/V) water. A portion of the precipitate was dried at 70° C. for 24 hours and weighed; 11.2 grams of magnetic iron oxide were formed.

It is to be noted that throughout this procedure the magnetic iron oxide particles, because of their superparamagnetic properties, never became permanently magnetized despite repeated exposure to magnetic fields. Consequently, only mild agitation was required to resuspend the particles during the water washings and methanol replacement treatment.

7.2. Silanization

The magnetic iron oxide particles (see Section 7.1.) suspended in 250 mls of methanol containing approximately 1% (V/V) water were placed in a Virtis 23 homogenizer (Virtis Company, Inc., Gardiner, NY). Two grams of orthophosphorous acid (Fisher Scientific Co., Pittsubrgh, PA) and 10 mls of p-aminophenyltrimethoxysilane (A-7025, Petrarch Systems, Inc., Bristol, PA) were added. In an alternative protocol, 5 mls of glacial acetic acid have been substituted for the 2 gms of orthophosphorous acid. The mixture was homogenized at 23,000 rpm for 10 minutes and at 9,000 rpm for 120 minutes. The contents were poured into a 500 ml glass beaker containing 200 mls of glycerol and heated on a hot plate until a temperature of 160°–170° C. was reached. The mixture was allowed to cool to room temperature. Both the heating and cooling steps were performed under nitrogen with stirring. The glycerol particle slurry (about 200 mls in volume) was poured into 1.5 liters of water in a 2 liter beaker; the particles were washed exhaustively (usually four times) with water according to the technique described in section 7.1.

This silanization procedure was performed with other silanes, including 3-aminopropyltrimethoxysilane, N-2-aminoethyl-3-aminopropyltrimethoxysilane, n-dodecyltriethoxysilane and n-hexyltrimethoxysilane (A-0800, A-0700, D-6224 and H-7334, respectively, Petrarch Systems, Inc., Bristol, PA).

As an alternative to the above silanization procedure, silane has also been deposited on superparamagnetic iron oxide (as prepared in Section 7.1) from acidic aqueous solution. Superparamagnetic iron oxide with $Fe^{2+}$/$Fe^{3+}$ ratio of 2 was washed with water as described in Section 7.1. The transfer to methanol was omitted. One gram of particles (about 20 mls of settled particles) was mixed with 100 mls of a 10% solution of 3-aminopropyl-trimethoxysilane in water. The pH was adjusted to 4.5 with glacial acetic acid. The mixture was heated at 90°–95° C. for 2 hours while mixing with a metal stir-blade attached to an electric motor. After cooling, the particles were washed 3 times with water (100 mls), 3 times with methanol (100 mls) and 3 times with water (100 mls), and the presence of silane on the particles was confirmed.

7.3. Physical Characteristics of Silanized Magnetic Particles

The mean particle diameter as measured by light scattering and the surface area per gram as measured by nitrogen gas adsorption for p-aminophenyl silanized, 3-aminopropyl silanized, and N-2-aminoethyl-3-aminopropyl silanized particles are summarized in Table IV. The particle surface area is closely related to the capacity of the particles to bind protein; as much as 300 mg/gm of protein can be coupled to the N-2-aminoethyl-3-aminopropyl silanized particle, far higher than previously reported values of 12 mg protein/gm of particles [Hersh and Yaverbaum, Clin. Chem. Acta 63: 69 (1975)]. For comparison, the surface areas per gram for two hypothetical spherical particles of silanized magnetite are listed in Table IV. The density of the hypothetical particles was taken to be 2.5 gm/cc, an estimate of the density of silanized magnetite particles. The diameter of each hypothetical particle was taken to be the mean diameter of the particles of the invention next to which entries for the hypothetical particle is listed. Observe that the surface area per gram of the particles of the invention as measured by nitrogen gas absorption is for greater than the calculated surface area per gram for perfect spheres of silanized magnetite of the same diameter. The greater surface area per gram of the particles of the invention indicates that the particles of the invention have a porous or otherwise open structure. Hypothetical perfect spheres of silanized magnetite having a diameter of $0.01\mu$ have calculated surface area per gram of about 120 $m^2$/gm.

TABLE IV
CHARACTERISTICS OF SILANIZED MAGNETIC PARTICLES

| Silane | Mean Diam.[1] ($\mu$) | Measured Surf. Area[2] ($m^2$/gm) | Hypoth. Surf. Area[3] ($m^2$/gm) |
|---|---|---|---|
| N—2 aminoethyl-3-aminopropyl | 0.561 | 140 | 4.3 |
| p-aminophenyl | 0.803 | NM[4] | — |
| 3-aminopropyl | 0.612 | 122 | 3.9 |

[1]Diameter (in microns) was measured by light scattering on a Coulter N-4 Particle Size Analyzer.
[2]Surface area was measured by $N_2$ gas adsorption.
[3]Calculated surface area per gram for a perfect sphere with a density at 2.5 gm/cc.
[4]Not Measured.

Because the mean diameters of the silanized magnetic particles produced by the procedures of Sections 7.1 and 7.2 are considerably smaller than the diameters of other magnetic particles described in the literature, they exhibit slower gravimetric settling times than those previously reported. For instance, the settling time of the particles described herein is approximately 150 minutes in contrast to settling times of: (a) 5 minutes for the particles of Hersh and Yaverbaum, [Clin. Chem. Acta 63: 69 (1975)], estimated to be greater than $10\mu$ in diameter; and (b) less than 1 minute for the particles of Robinson et al. [Biotech. Bioeng. XV:603 (1973)] which are 50–160$\mu$ in diameter.

The silanized magnetic particles of this invention are characterized by very slow rates of gravimetric settling as a result of their size and composition; nevertheless they respond promptly to weak magnetic fields. This is depicted in FIG. 1 where the change in turbidity over time of a suspension of silanized magnetic particles resulting from spontaneous particle settling in the absence of a magnetic field is compared to the change in the turbidity produced in the presence of a samarium-cobalt magnet. It can be seen that after 30 minutes the turbidity of the suspension has changed only slightly more than 10% in the absence of a magnetic field. However, in the presence of a weak magnetic field, the turbidity of the particle suspension drops by more than 95% of its original value within 6 minutes. In another experiment, a decrease in turbidity of only about 4% in 30 minutes was observed.

Figure 2:
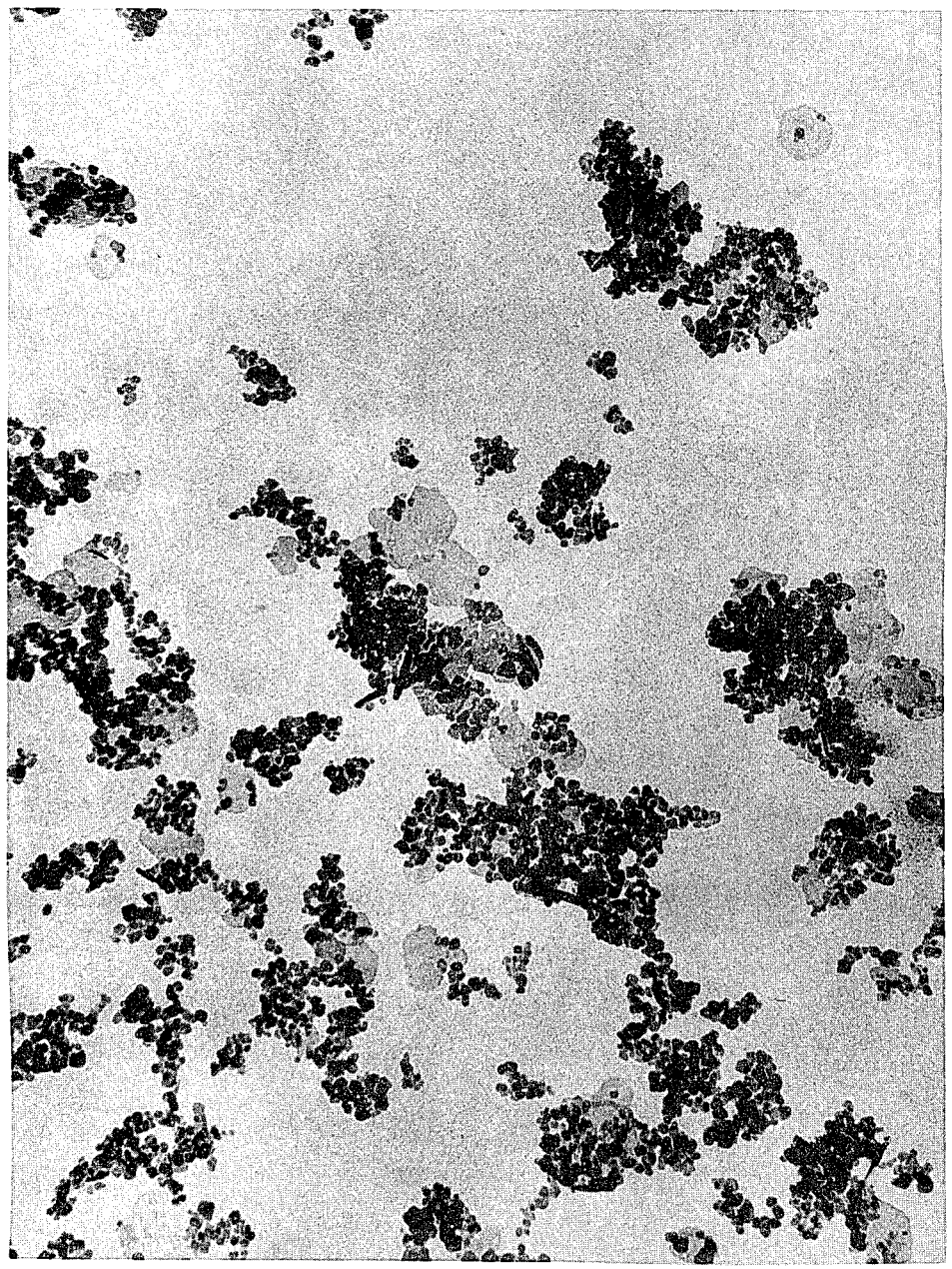
FIG. 2 is a photomicrograph of superparamagnetic particles silanized with 3-aminopropyltrimethoxy silane.

A photomicrograph of superparamagnetic particles silanized with 3-aminotrimethoxysilanes ("SIN" particles) is shown in FIG. 2. It can be seen that the particles vary in shape and size and that they are made up of a groups or clusters of individual superparamagnetic crystals (less than 300 A) which appear roughly spherical in shape.

7.4. Coupling of Aminophenyl Magnetic Particles to Antibodies to Thyroxine

First, thyroxine ($T_4$) antiserum was prepared as follows: 5.0 mls of serum of sheep immunized with $T_4$ (obtained from Radioassay Systems Laboratories, Inc., Carson, CA) were added to a 50 ml centrifuge tube. Two 5.0 ml aliquots of phosphate buffered saline (PBS) were added to the tube followed by 15 mls of 80% saturated ammonium sulfate, pH 7.4, at 4° C. After mixing, the tube was stored at 4° C. for 90 minutes. The mixture was then centrifuged at 3,000 rpm for 30 minutes at 4° C. The supernatant fraction was decanted and the pellet resuspended and dissolved to clarity in 5.0 mls of PBS. The $T_4$ antiserum preparation (1:2 in PBS) was dialyzed against PBS, transferred from the dialysis tubing to a 50 ml centrifuge tube to which 40 mls of PBS were added, bringing the total volume to 50 mls. The T4 antiserum preparation (1:10 in PBS) was refrigerated until used for coupling.

To 1740 mg of p-aminophenyl silanized particles in 100 mls of 1N hydrochloric acid (HCl), 25 mls of 0.6 M sodium nitrite (NaNO2) were added. The NaNO2 was added slowly below the surface of the particle/HCl mixture while maintaining the temperature between 0° and 5° C. with care taken to avoid freezing. After 10 minutes, the mixture was brought to pH 7.5–8.5 by addition of 65 mls of 1.2 M NaOH and 18 mls of 1 M sodium bicarbonate (NaHCO3), still maintaining temperature at 0° to 5° C. Then, 50 mls of PBS containing 100 mg of the gamma globulin fraction of sheep serum containing antibodies to thyroxine (the T4 antiserum preparation described supra) were added. The pH was maintained between 7.5–8.5 while the mixture was incubated for 18 hours at 0° to 5° C. The antibody-coupled particles were washed exhaustively with 0.1 M sodium phosphate buffer, pH 7.2 (3 times), 1 M NaCl, methanol, 1 M NaCl and 0.1 M sodium phosphate buffer again. Wash steps were repeated twice or more. All washes were performed by dispersing the particles and magnetically separating them as described in section 7.1. After washing, the particles were resuspended in PBS and incubated overnight at 50° C. The particles were washed in methanol, 1 M NaCl and 0.1 M sodium phosphate buffer as before, and twice in Free T4 Tracer Buffer. The particles were resuspended in Free T4 Tracer Buffer and stored at 4° C. until used for radioimmunoassay.

7.5. Magnetic Particle Radioimmunoassay for Thyroxine

The quantity of antibody-coupled magnetic particles to be used in the thyroxine radioimmunoassay (RIA) was determined empirically using the following RIA procedure:

Ten microliters ($\mu$ls) of standard were pipetted into 12×75 mm polypropylene tubes followed by 500 $\mu$ls of tracer and 100 $\mu$ls of magnetic particles. After vortexing, the mixture was incubated at 37° C. for 15 minutes after which time the tubes were placed on a magnetic rack for 10 minutes. The rack consisted of a test tube holder with a cylindrical "button" magnet (Incor 18, Indiana General Magnetic Products Corp., Valparaiso, IN) at the bottom of each tube. The magnetic particles with antibody and bound tracer were pulled to the bottom of the tubes allowing the unbound tracer to be removed by inverting the rack and pouring off supernatants. Radioactivity in the pellet was determined on a Tracor 1290 Gamma Counter (Tracor Analytic, Inc., Elk Grove Village, IL).

The reagents used in the assay were as follows:

Standards were prepared by adding T4 to T4-free human serum. T4 was removed from the serum by incubation of serum with activated charcoal followed by filtration to remove the charcoal according to the method of Carter [Clin. Chem 24, 362 (1978)]. The tracer was $^{125}$I-thyroxine purchased from Cambridge Medical Diagnostics (#155) and was diluted into 0.01 M Tris buffer containing 100 $\mu$g/ml bovine serum albumin, 10 $\mu$g/ml salicylate, 50 $\mu$g/ml 8-amilinonaphthalene-8-sulfonic acid at pH 7.4. Magnetic particles at various concentrations in phosphate buffered saline (PBS) with 0.1% bovine serum albumin were used in the RIA to determine a suitable concentration of particles for T4 measurements. A quantity of magnetic particles of approximately 50 $\mu$g per tube was chosen for the RIA. This amount permitted good displacement of tracer from the antibody for the desired concentration range of T4 (0–32 $\mu$g/dl).

Having thus determined the optimal quantity, the RIA procedure described supra was performed using approximately 50 $\mu$g per tube of magnetic particles to construct a radioimmunoassay standard curve for T4. The data obtained from the RIA is presented in Table V.

TABLE V

| RIA STANDARD CURVE FOR T4 | |
|---|---|
| T4 Concentration | cpm (average of 2 tubes) |
| 0 $\mu$g/dl | 36763 |
| 2 $\mu$g/dl | 24880 |
| 4 $\mu$g/dl | 18916 |
| 8 $\mu$g/dl | 13737 |
| 16 $\mu$g/dl | 10159 |
| 32 $\mu$g/dl | 7632 |
| Total | 69219 |

7.6. Magnetic Particle Radioimmunoassay for Theophylline

Rabbit anti-theophylline antibodies were prepared and coupled to p-aminophenyl silanized particles according to methods similar to those described in Section 7.4. The anti-theophylline antibody-coupled magnetic particles were used in a radioimmunoassay with the following protocol: 20 $\mu$ls of theophylline standard (obtained by adding theophylline to theophylline-free human serum), 100 $\mu$ls of $^{125}$I-theophylline tracer (obtained from Clinical Assays, Cambridge, MA), and 1 ml of antibody-coupled magnetic particles were vortexed. After a 15 minute incubation at room temperature, a 10 minute magnetic separation was employed. A standard curve was constructed and the data obtained are shown in Table VI.

TABLE VI

| RIA STANDARD CURVE FOR THEOPHYLLINE | |
|---|---|
| Theophylline Concentration | cpm (average of 2 tubes) |
| 0 $\mu$g/dl | 35061 |
| 2 $\mu$g/dl | 28217 |
| 8 $\mu$g/dl | 19797 |
| 20 $\mu$g/dl | 13352 |
| 60 $\mu$g/dl | 8148 |
| Total | 52461 |

7.7. Effect of Variation of $Fe^{2+}/Fe^{3+}$ Ratio of Magnetic Particles on T4 Radioimmunoassay Magnetic iron oxides were made according to the crystallization procedure of Section 7.1 by maintaining constant molar amounts of iron but varying the $Fe^{2+}/Fe^{3+}$ ratio from 4 to 0.5. These particles were silanized, coupled to anti-T4 antibodies and used in the T4 RIA, as in Sections 7.2, 7.4 and 7.5, respectively. The variation of $Fe^{2+}/Fe^{3+}$ ratio did not substantially affect the performance of these magnetic particles in the T4 RIA as shown in Table VII.

TABLE VII

| T4 RIA STANDARD CURVES USING MAGNETIC PARTICLES WITH VARIED $Fe^{2+}/Fe^{3+}$ RATIOS | | |
|---|---|---|
| | cpm (average of 2 tubes) | |
| T4 Concentration | $Fe^{2+}/Fe^{3+} = 4$ | $Fe^{2+}/Fe^{3+} = 0.5$ |
| 0 $\mu$g/dl | 35633 | 35642 |

TABLE VII-continued

T4 RIA STANDARD CURVES USING MAGNETIC PARTICLES WITH VARIED $Fe^{2+}/Fe^{3+}$ RATIOS

| T4 Concentration | cpm (average of 2 tubes) | |
|---|---|---|
| | $Fe^{2+}/Fe^{3+} = 4$ | $Fe^{2+}/Fe^{3+} = 0.5$ |
| 1 μg/dl | 31681 | 33139 |
| 2 μg/dl | 30572 | 30195 |
| 4 μg/dl | 24702 | 25543 |
| 8 μg/dl | 18680 | 19720 |
| 16 μg/dl | 12803 | 11625 |
| 32 μg/dl | 10012 | 8005 |
| Total | 77866 | 75636 |

7.8. Coupling of Carboxylic Acid-Terminated Magnetic Particles to $B_{12}$ Binding Protein

7.8.1 Preparation of Carboxylic Acid-Terminated Magnetic Particles

A superparamagnetic iron oxide was made by the procedure described in Section 7.1 and silanized as in Section 7.2 with 3-aminopropyltrimethyoxysilane instead of the aminophenyl silane. The amino group of the silane was then reacted with glutaric anhydride to convert the termination from an amine to carboxylic acid. The conversion of the termination was accomplished as follows: five grams of aminopropyl silanized particles in water were washed four times with 1.5 liters of 0.1 M $NaHCO_3$ using the washing procedure of Section 7.1. The volume was adjusted to 100 mls and 2.85 gm glutaric anhydride was added. The particles were washed two times and the reaction with glutaric anhydride was repeated. The carboxylic acid-terminated magnetic particles were washed five times with water to prepare them for reaction with protein.

7.8.2. Carbodiimide Coupling of $B_{12}$ Binding Protein and Human Serum Albumin to Carboxylic Acid-Terminated Magnetic Particles To 50 mg of carboxy-terminated magnetic particles in 1 ml of water were added 4 mg of 3-(3 dimethylaminopropyl)-carbodiimide. After mixing by shaking for 2 minutes, 0.05 mg of $B_{12}$ binding protein (intrinsic factor (IF) from hog gut obtained from Dr. R. H. Allen, Denver, CO) and 0.75 mg of human serum albumin (HSA, obtained from Sigma Chemical Co., A-8763) were added to 0.30 ml in water. The pH was adjusted to pH 5.6 and maintained by the addition of 0.1 N HCl or 0.1 N NaOH for three hours. The particles were then washed with 10 mls of 0.1 M Borate with 0.5 M NaCl pH 8.3, 10 mls of phosphate buffered saline (PBS) with 0.1% HSA, and 10 mls of distilled water employing the magnetic separation technique as in Section 7.1. Particles were washed three times with PBS and stored in PBS until use.

7.9. Magnetic Particle Competitive Binding Assay for Vitamin $B_{12}$

Using the IF- and HSA-coupled magnetic particles made by the method of Section 7.7, a titering of the particles was performed to ascertain the quantity of particles needed in a competitive binding assay for vitamin $B_{12}$ ($B_{12}$). The following assay protocol was used:

100 μls of standard and 1000 μls of tracer buffer were added to 12×75 mm polypropylene tubes. The mixtures were placed into a boiling water bath for 15 minutes to effect denaturation of binding proteins in human serum samples. Then 100 μls of various concentrations of magnetic particles in phosphate buffer were added to determine the optimal quantity of particles for assaying $B_{12}$ concentrations between 0 and 2000 picogram/ml (pg/ml). After incubation of the mixtues for 1 hour at room temperature, a magnetic separation of bound and free $B_{12}$ was performed according to the procedure of and using the magnetic rack described in Section 7.5. Radioactivity in the pellets was then counted on a Tracor 1290 Gamma Counter (Tracor Analytic, Inc., Elk Grove Village, IL).

The reagents used in the assay were as follows:

$B_{12}$ standards were obtained from Corning Medical and Scientific, Division of Corning Glass Works, Medfield, MA #474267. They are made with $B_{12}$-free human serum albumin in PBS and sodium azide added as a preservative. The tracer was $^{57}Co$-$B_{12}$ (vitamin $B_{12}$ tagged with radioactive cobalt) from Corning Medical and Scientific, Division of Corning Glass Works, Medfield, MA, #474287. The tracer is in a borate buffer pH 9.2, containing 0.001% potassium cyanide and sodium azide. Magnetic particles were diluted in PBS at various concentrations to determine the quantity of particles needed to measure $B_{12}$ concentrations between 0 and 2000 pg/ml.

A quantity of magnetic particles of approximately 50 μg/tube was selected and was used in the $B_{12}$ competitive binding assay supra to construct a standard curve; the data are presented in Table VIII.

TABLE VIII $B_{12}$ COMPETITIVE BINDING ASSAY STANDARD CURVE

| $B_{12}$ Concentration | cpm (average of 2 tubes) |
|---|---|
| 0 pg/ml | 5523 |
| 100 pg/ml | 5220 |
| 250 pg/ml | 4169 |
| 500 pg/ml | 3295 |
| 1000 pg/ml | 2278 |
| 2000 pg/ml | 1745 |
| Total | 16515 |

7.10. Coupling of Magnetic Particles Coated With Aminoethyl-3-Aminopropyl Silane to Proteins

7.10.1. Coupling of N-2-Aminoethyl-2-Aminopropyl Magnetic Particles to Antibodies to Triiodothyronine Six-tenths of a gram of N-2-aminoethyl-3-aminopropyl magnetic particles (abbreviated "DIN" particles for "dinitrogen", signifying that the particles have a N/Si ratio of 2) prepared as in Section 7.2. were resuspended in water. The particles were washed once in water and then twice with 30 mls of 0.1 M phosphate buffer, pH 7.4 with magnetic separations between washings. After suspending the washed particles in 15 mls of 0.1 M phosphate, 15 mls of a 5% (V/V) solution of glutaraldehyde, formed by diluting 25% glutaraldehyde (G- 5882, Sigma Chemical Co., St. Louis, MO) with 0.1 M phosphate, were added. The particles were mixed for 3 hours at room temperature by gently rotating the reaction vessel. Unreacted glutaraldehyde was washed away with 5 additions of 30 mls of 0.1 M phosphate buffer. The glutaraldehyde activated particles were then resuspended in 15 mls of 0.1 M phosphate.

Triiodothyronine ($T_3$) antiserum (1.6 mls, obtained by immunizing rabbits with $T_3$- BSA conjugates) was added to the activated particles and stirred on a wheel mixer at room temperature for 16 to 24 hours. The $T_3$ antibody-coupled particles were washed once with 30 mls of 0.1 M phosphate and suspended in 15 mls of 0.2 M glycine solution in order to react any unreacted aldehyde groups. The suspension was mixed by shaking for 25 minutes. The antibody-coupled particles were washed with 30 mls of 0.1 phosphate, 30 mls of ethanol and twice with 150 mls of PBS with 0.1% bovine serum albumin (BSA). They were resuspended in PBS, 1% BSA and stored at 4° C. until used for RIA for $T_3$.

7.10.2. Coupling of N-2-Aminoethyl-3-Aminopropyl Magnetic Particles to Antibodies to Thyroid Stimulating Hormone The coupling procedure of Section 6.10.1 was followed with minor modifications. Twenty grams of DIN particles were washed three times with 1.5 liters of methanol prior to glutaraldehyde activation. Glutaraldehyde activation was performed as in Section 7.10.1. with adjustments for scale.

A goat gamma globulin fraction containing antibodies to human thyroid stimulating hormone (TSH) was coupled to the DIN particles rather than whole antisera. Fractionation was accomplished by precipitation of gammaglobulins with 40% ammonium sulfate followed by dialysis against PBS. Approximately 4 grams of protein (200 mls at 20 mg/ml) were coupled. Complete attachment of protein was evident by the absence of optical density at 280 nm in the supernatant after coupling. This indicated the attachment of about 20 mg of protein per gram of particles. The particles were then washed three times with 1.5 liters of 1 M NaCl, three times with PBS and incubated at 50° C. overnight. Particles were then washed 3 more times in PBS/BSA and titered for use in the TSH assay.

7.11. Magnetic Particle Radioimmunoassay for Triiodothyronine

The quantity of particles to be used in the $T_3$ RIA was determined in the following assay:

Standards were prepared by adding $T_3$ to $T_3$-free human serum as with $T_4$ (see Section 7.5.)

Tracer was $^{125}IT_3$ from Corning Medical and Scientific, Division of Corning Glass Works, Medfield, MA (#47106).

Magnetic particles were diluted to various concentrations in PBS-BSA to determine the quantity of particles needed.

The assay protocol was as follows: 50 μls of standard, 100 μls of tracer and 800 μls of DIN magnetic particles were pipetted into 12×75 mm polypropylene tubes. After vortexing, the tubes were incubated for 2 hours at room temperature. The assay was terminated by magnetic separation. By titering the quantity of particles in the assay with a 0 ng/ml standard, a quantity of 30 μg/tube was deemed to be optimal for the assay protocol. Table IX shows the $T_3$ RIA standard curve data obtained with these particles.

TABLE IX

| RIA STANDARD CURVE FOR $T_3$ | |
|---|---|
| $T_3$ Concentration | cpm (average of 2 tubes) |
| 0.0 ng/ml | 17278 |
| 0.25 ng/ml | 15034 |
| 0.50 ng/ml | 13456 |
| 1.00 ng/ml | 12127 |
| 2.00 ng/ml | 8758 |
| 4.00 ng/ml | 5776 |
| 8.00 ng/ml | 3897 |
| Total | 26946 |

7.12. Magnetic Particle Radioimmunoassay for Thyroid Stimulating Hormone

The quantity of particles to be used in the TSH RIA was determined in the following assay:

Standards were in normal human serum (Corning Medical and Scientific, #47186, Medfield, MA).

Tracer was $^{125}I$-rabbit anti-TSH antibody in PBS (Corning Medical and Scientific, #474185, Medfield, MA).

Magnetic particles were diluted to various concentrations in PBS-BSA to determine the quantity of particles needed.

The assay protocol was as follows: 100 μls of standard and 100 μls of tracer were pipetted into 12×75 mm polypropylene tubes, vortexed, and incubated for 3 hours at room temperature. Magnetic particles (500 μls) were added and the mixture was vortexed and incubated for 1 hour at room temperature. 500 μls of water were added and the usual magnetic separation was employed to separate bound from unbound tracer. In the presence of TSH, a sandwich is formed between magnetic antibody (goat anti-TSH antibody, see Section 7.10.1.) TSH and tracer $^{125}I$-antibody (rabbit anti-TSH antibody). Thus, increasing concentrations of analyte (TSH) increase the amount of bound radioactivity. Table X shows the TSH RIA standard curve data obtained by this procedure.

TABLE X

| RIA STANDARD CURVE FOR TSH | |
|---|---|
| TSH Concentration | cpm |
| 0    μIU/ml* | 1615 |
| 1.5  μIU/ml* | 2309 |
| 3.0  μIU/ml* | 3014 |
| 6.0  μIU/ml* | 4448 |
| 15.0 μIU/ml* | 7793 |
| 30.0 μIU/ml* | 11063 |
| 60.0 μIU/ml* | 15030 |
| Total | 45168 |

*μIU = micro International Units

7.13. Coupling of Magnetic Particles Coated with N-2-Aminoethyl-3-Aminopropyl Silane to Enzymes by Use of Glutaraldehyde Magnetic particles (1 gm) were activated with glutaraldehyde as in Section 7.10.1. After washing, the particles were resuspended in 15 mls of PBS. Then 3 mls of particles (2 gm) were mixed with 5 mg of alkaline phosphatase (Sigma Chemical Company, p-9761) or 5 mg of β-galactosidase (Sigma Chemical Company, 5635) dissolved in 2.0 mls of PBS. The coupled particles were washed with glycine and then washed 5 times with PBS and resuspended in PBS with 0.1% BSA.

Enzyme assays for magnetic alkaline phosphatase activity was performed as follows:

To a 3 ml cuvette 3 mls of 0.05 M Tris-HCl were added, pH 8.0, with 3 mM p-nitrophenyl-phosphate. Then 100 μls of diluted magnetic particles with coupled alkaline phosphatase were added. The increase in optical density at 410 nm was recorded.

Enzyme assay for magnetic β-galactosidase activity was performed as follows:

To a 3 ml cuvette 3 mls of 0.1 M phosphate were added, pH 7.4, with 0.01 M mercaptoethanol and 0.005 M O-nitrophenyl-β-O-galactopyranoside. Then 100 μls of diluted magnetic particles coupled to β-galactosidase were added. The increase in optical density at 410 nm was recorded.

It is apparent that many modifications and variations of this invention as hereinabove set forth may be made without departing from the spirit and scope thereof. The specific embodiments described are given by way of example only and the invention is limited only by the terms of the appended claims.

We claim:

1. A coupled magnetically-responsive particle comprising a magnetic metal oxide core generally surrounded by a coat of polymeric silane to which molecules of at least one type of bioaffinity adsorbent are covalently coupled, a mass of the uncoupled particles being dispersable in aqueous media to form an aqueous dispersion having (a) a fifty-percent-turbidity-decrease settling time of greater than about 1.5 hours in the absence of a magnetic field, and (b) a ninety-five-percent-turbidity-decrease separation time of less than about 10 minutes in the presence of a magnetic field, the magnetic field being applied to the aqueous dispersion by bringing a vessel containing a volume of the dispersion into contact with a pole face of a permanent magnet, the permanent magnet having a volume which is less than the volume of the aqueous dispersion in the vessel.

2. A coupled magnetically-responsive particle comprising a superparamagnetic iron oxide core generally surrounded by a coat of polymeric silane to which molecules of at least one type of bioaffinity adsorbent are covalently coupled, the iron oxide core including a group of crystals of iron oxide, the uncoupled particle having a mean diameter as measured by light scattering between about $0.1\mu$ and about $1.5\mu$ and a surface area as measured by nitrogen gas adsorption of at least about 100 $m^2/gm$, a mass of the uncoupled particles being dispersable in aqueous media to form an aqueous dispersion having (a) a fifty-percent-turbidity-decrease settling time of greater than about 1.5 hours in the absence of a magnetic field, and (b) a ninety-five-percent-turbidity-decrease separation time of less than about 10 minutes in the presence of a magnetic field, the magnetic field being applied to the aqueous dispersion by bringing a vessel containing a volume of the dispersion into contact with a pole face of a permanent magnet, the permanent magnet having a volume which is less than the volume of the aqueous dispersion in the vessel.

3. A coupled magnetically-responsive particle comprising a ferromagnetic metal oxide core generally surrounded by a coat of polymeric silane to which molecules of at least one type of bioaffinity adsorbent are covalently coupled, the metal oxide core including a group of crystals of metal oxide, the uncoupled particle having a mean diameter as measured by light scattering between about $0.1\mu$ and about $1.5\mu$ and a surface area as measured by nitrogen gas adsorption of at least about 100 $m^2/gm$, a mass of the uncoupled particles being dispersable in aqueous media to form an aqueous dispersion having (a) a fifty-percent-turbidity-decrease settling time of greater than about 1.5 hours in the absence of a magnetic field, and (b) a ninety-five-percent-tubidity-decrease separation time of less than about 10 minutes in the presence of a magnetic field, the magnetic field being applied to the aqueous dispersion by bringing a vessel containing a volume of the dispersion into contact with a pole face of a permanent magnet, the permanent magnet having a volume which is less than the volume of the aqueous dispersion in the vessel.

4. The coupled magnetically-responsive particle of claim 1, 2 or 3 wherein the bioaffinity adsorbent is selected from the group consisting of antibodies, antigens, haptens, enzymes, apoenzymes, enzymatic substrates, enzymatic inhibitors, cofactors, binding proteins, carrier proteins, compounds bound by binding proteins, compounds bound by carrier proteins, lectins, monosaccharides, polysaccharides, hormones, receptors, repressors and inducers.

5. The coupled magnetically-responsive particle of claim 2 or 3 wherein the covalently coupled bioaffinity adsorbent is an antibody selected from the group consisting of anti-thyroxine, anti-triiodothyronine, anti-thyroid stimulating hormone, anti-thyroid binding globulin, anti-thyroglobulin, anti-digoxin, anti-cortisol, anti-insulin, anti-theophylline, anti-vitamin $B_{12}$, anti-folate, anti-ferritin, anti-human chorionic gonadotropin, anti-follicle stimulating hormone, anti-leuteinizing hormone, anti-progesterone, anti-testosterone, anti-estriol, anti-estradiol, anti-prolactin, anti-human placental lactogen, anti-gastrin and anti-human growth hormone antibodies.

6. The coupled magnetically-responsive particle of claim 2 wherein the coat of polymeric silane is a coat of p-aminophenyltrimethoxysilane polymer and wherein the bioaffinity adsorbents are anti-thyroxine antibodies, which antibodies are covalently coupled to the coat of polymeric silane by diazotization.

7. The coupled magnetically-responsive particle of claim 2 wherein the coat of polymeric silane is a coat of p-aminophenyltrimethoxysilane polymer and wherein the bioaffinity adsorbents are anti-theophylline antibodies, which antibodies are covalently coupled to the coat of polymeric silane by diazotization.

8. The coupled magnetically-responsive particle of claim 2 wherein the coat of polymeric silane is a coat of carboxylic-acid terminated glutaric-anhydride-treated 3-aminopropyltrimethoxysilane polymer and wherein the bioaffinity adsorbents are molecules of vitamin $B_{12}$ binding protein, which molecules of vitamin $B_{12}$ binding protein are covalently coupled to the coat of polymeric silane by carbodiimide coupling.

9. The coupled magnetically-responsive particle of claim 2 wherein the coat of polymeric silane is a coat of N-2-aminoethyl-3-aminopropylsilane polymer and wherein the bioaffinity adsorbents are anti-triiodothyronine antibodies, which antibodies are covalently coupled to the coat of polymeric silane by glutaraldehyde coupling.

10. The coupled magnetically-responsive particle of claim 2 wherein the coat of polymeric silane is a coat of N-2-aminoethyl-3-aminopropylsilane polymer and wherein the bioaffinity adsorbents are anti-thyroid stimulating hormone antibodies, which antibodies are covalently coupled to the coat of polymeric silane by glutaraldehyde coupling.

11. The coupled magnetically-responsive particle of claim 2 wherein the coat of polymeric silane is a coat of N-2-aminoethyl-3-aminopropylsilane polymer and wherein the bioaffinity adsorbents are enzymes selected from the group consisting of alkaline phosphatase and $\beta$-galactosidase, which enzymes are covalently coupled to the coat of polymeric silane by glutaraldehyde coupling.

* * * * *